United States Patent
Ganeshan et al.

(10) Patent No.: US 12,094,580 B2
(45) Date of Patent: Sep. 17, 2024

(54) NEURAL NETWORK FORCE FIELD COMPUTATIONAL TRAINING ROUTINES FOR MOLECULAR DYNAMICS COMPUTER SIMULATIONS

(71) Applicant: Robert Bosch GmbH, Stuttgart (DE)

(72) Inventors: Karthik Ganeshan, State College, PA (US); Karim Gadelrab, Boston, MA (US); Mordechai Kornbluth, Brighton, MA (US); Jonathan Mailoa, Cambridge, MA (US)

(73) Assignee: Robert Bosch GmbH, Stuttgart (DE)

( * ) Notice: Subject to any disclaimer, the term of this patent is extended or adjusted under 35 U.S.C. 154(b) by 453 days.

(21) Appl. No.: 17/484,448

(22) Filed: Sep. 24, 2021

(65) Prior Publication Data

US 2023/0095631 A1    Mar. 30, 2023

(51) Int. Cl.
  *G16C 20/70*    (2019.01)
  *G06N 3/08*    (2023.01)
  *G16C 60/00*    (2019.01)

(52) U.S. Cl.
  CPC ............ *G16C 20/70* (2019.02); *G06N 3/08* (2013.01); *G16C 60/00* (2019.02)

(58) Field of Classification Search
  CPC ........ G16C 20/70; G16C 20/50; G16C 20/80; G16C 60/00; G16C 10/00; G06N 3/04; G06N 3/08; G06N 3/044; G06N 3/0464; G06N 3/088; G06N 7/01; G06N 10/00; G06N 20/00; G16B 15/00; G16B 5/20; B01J 2219/007; Y10S 128/925

(Continued)

(56) References Cited

U.S. PATENT DOCUMENTS

2020/0167439 A1* 5/2020 Mailoa ................. G16C 60/00
2022/0100931 A1* 3/2022 Kornbluth ............ G06V 10/82

FOREIGN PATENT DOCUMENTS

CN    111951899 A  * 11/2020  ............ G06N 3/002
CN    112489732 A  *  3/2021  ......... G06F 16/9024

OTHER PUBLICATIONS

Park et al., "Accurate and scalable multi-element graph neural network force field and molecular dynamics with direct force architecture," arXiv preprint arXiv:2007.14444, 2020, pp. 1-33.

(Continued)

*Primary Examiner* — Jeffrey P Aiello
(74) *Attorney, Agent, or Firm* — Brooks Kushman P.C.

(57) ABSTRACT

A computational method for training a neural network force field (NNFF) configured to simulate molecular and/or atomic motion within a material system. The method includes the step of receiving molecular structure data of a molecule in the material system. The method also includes optimizing a geometry of the molecule using the molecular structure data and a density functional theory (DFT) simulation to obtain DFT optimized geometry data. The method further includes optimizing the geometry of the molecule using the molecular structure data and a classical force field (FF) simulation to obtain FF optimized geometry data. The method also includes outputting NNFF training data comprised of the DFT optimized geometry data and the FF optimized geometry data. The NNFF training data is configured to train an NNFF for simulating molecular and/or atomic molecular and/or atomic motion within the material system.

20 Claims, 8 Drawing Sheets

(58) Field of Classification Search
USPC .... 702/22, 19, 27, 30, 32, 182, 181, 179, 1, 702/189; 703/11, 2, 6, 13, 22; 706/45, 706/21, 15, 16, 25
See application file for complete search history.

(56) References Cited

OTHER PUBLICATIONS

Rappe et al., "UFF, a Full Periodic Table Force Field for Molecular Mechanics and Molecular Dynamics Simulations,". Journal of the American Chemical Society, 1992, vol. 114, No. 25, pp. 10024-10035.
Schutt et al., "SchNet: A continuous-filter convolutional neural network for modeling quantum interactions," arXiv preprint arXiv:1706.08566, 2017, pp. 1-11.
Schutt et al., "Quantum-chemical insights from deep tensor neural networks," Nature Communications, 2017, vol. 8, No. 13890, pp. 1-8, DOI: 10.1038/ncomms13890.
Van Duin et al., "ReaxFF: A Reactive Force Field for Hydrocarbons," The Journal of Physical Chemistry A, 2001, vol. 105, No. 41, pp. 9396-9409, DOI: 10.1021/jp004368u.
Vandermause et al., "On-the-fly active learning of interpretable Bayesian force fields for atomistic rare events," npj Computational Materials, 2020, vol. 6, No. 20, pp. 1-11, DOI: https://doi.org/10.1038/s41524-020-0283-z.

* cited by examiner

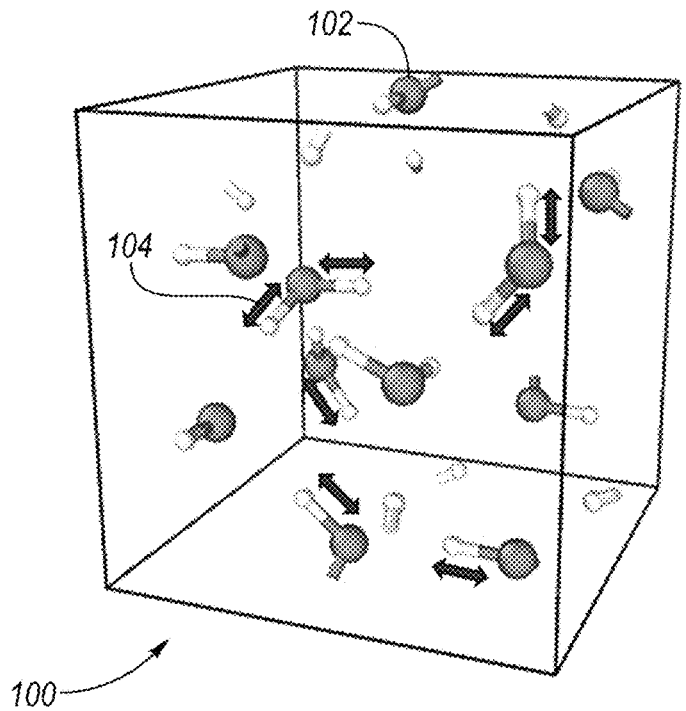
FIG. 3A
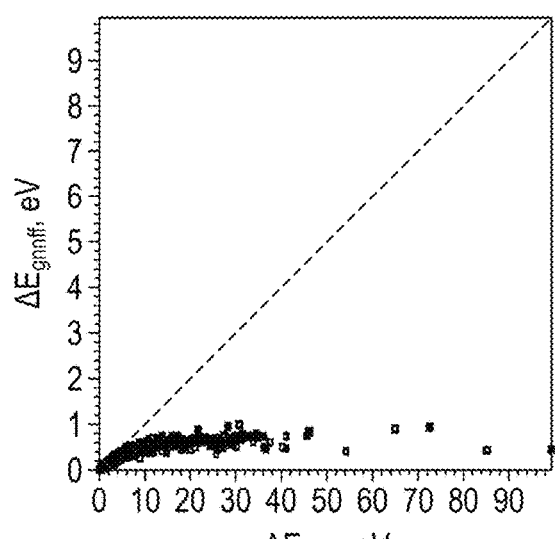 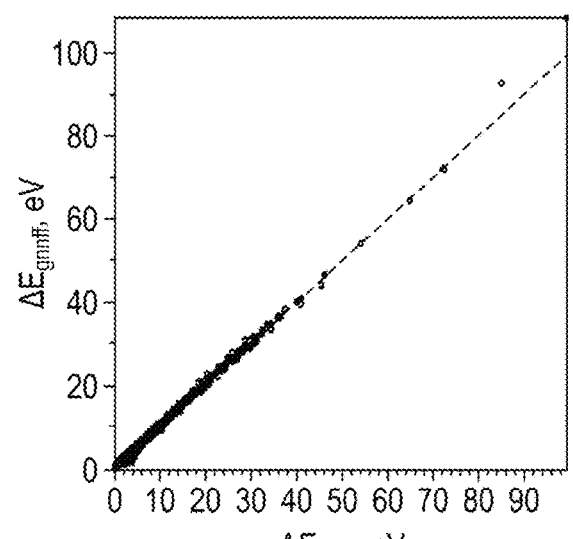
FIG. 3B        FIG. 3C

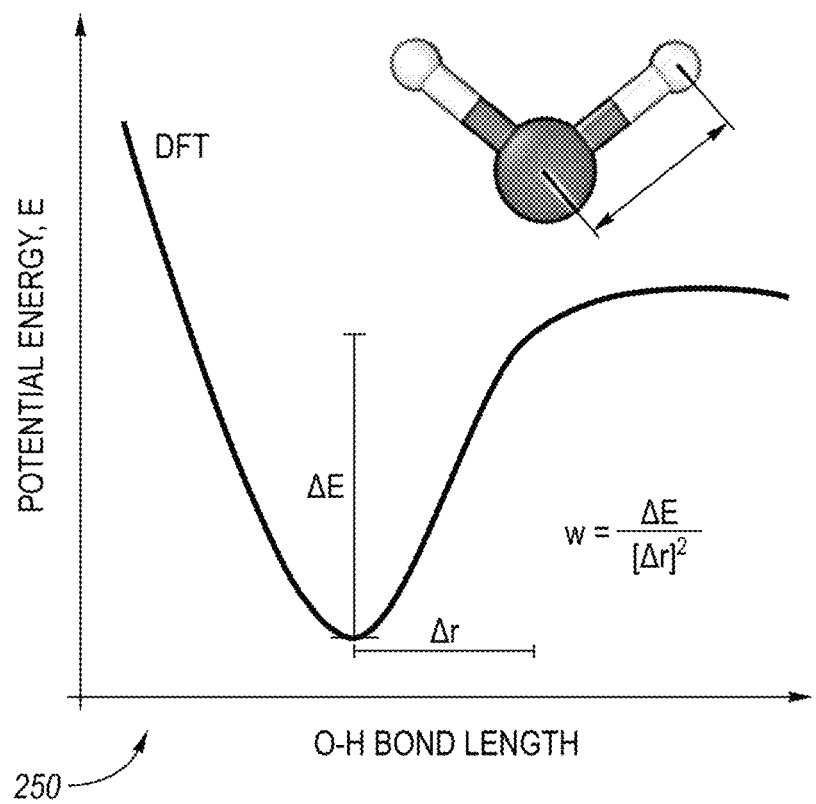
FIG. 6A
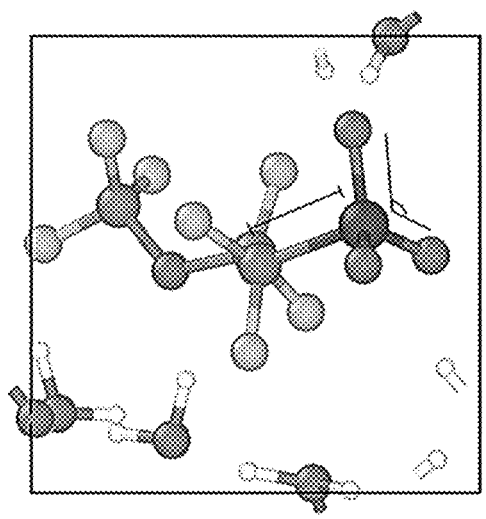 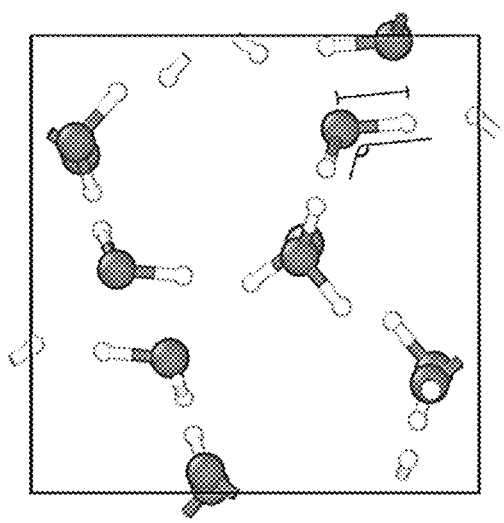
FIG. 6B          FIG. 6C

NEURAL NETWORK FORCE FIELD COMPUTATIONAL TRAINING ROUTINES FOR MOLECULAR DYNAMICS COMPUTER SIMULATIONS

TECHNICAL FIELD

This invention relates generally to neural network force field (NNFF) computational training routines used in molecular dynamics computer simulations for material systems, such as electrochemical and water filtration devices.

BACKGROUND

Molecular dynamics is a computational materials science methodology for simulating the motion of atoms in a material system at real operating pressure and temperature conditions. Methodologies exist to calculate the underlying atomic forces used in the simulation of the motion of atoms. One methodology is the ab-initio quantum mechanics approach. This approach is very accurate but is also very expensive because of the tremendous amount of computational resources necessary to apply the approach. While other approaches exist that consume less computational resources, these other approaches do not deliver as much accuracy.

SUMMARY

In a first embodiment, a computational process for training a neural network force field (NNFF) configured to simulate molecular and/or atomic motion within a material system is disclosed. The process includes the step of receiving molecular structure data of a molecule in the material system. The process also includes optimizing a geometry of the molecule using the molecular structure data and a density functional theory (DFT) simulation to obtain DFT optimized geometry data. The process further includes optimizing the geometry of the molecule using the molecular structure data and a classical force field (FF) simulation to obtain FF optimized geometry data. The process also includes outputting NNFF training data comprised of the DFT optimized geometry data and the FF optimized geometry data. The NNFF training data is configured to train the NNFF for simulating molecular and/or atomic motion within the material system. The steps of this computational process may be provided as operations associated with a non-transitory computer-readable medium tangibly embodying computer readable instructions for a software program. The software program is executable by a processor of a computing device to provide the operations. The non-transitory computer-readable medium may be implemented on a simulation computer(s) of a computer system.

In a second embodiment, a computational process for training a neural network force field (NNFF) configured to simulate molecular and/or atomic motion within a material system is disclosed. The computational process includes receiving molecular structure data of a molecule in the material system. The molecular structure data includes an irrational structure of the molecule. The computation process further includes solvating the irrational structure of the molecule using a classical FF simulation or an ab initio molecular dynamics (MD) simulation to obtain solvation trajectory data of the molecule. The process also includes outputting NNFF training data comprised of the solvation trajectory data. The NNFF training data is configured to train the NNFF for simulating molecular and/or atomic motion within the material system. The steps of this computational process may be provided as operations associated with a non-transitory computer-readable medium tangibly embodying computer readable instructions for a software program. The software program is executable by a processor of a computing device to provide the operations. The non-transitory computer-readable medium may be implemented on a simulation computer(s) of a computer system.

In a third embodiment, a computational process for training a neural network force field (NNFF) configured to simulate molecular and/or atomic motion within a material system is disclosed. The process includes receiving molecular structure data of a molecule in the material system. The molecular structure data is predicted from a density functional theory (DFT) simulation. The molecular structure data includes one or more tracked bonds, angles, and/or structures. The process further includes evaluating the molecular structure data to obtain geometry error data of the one or more tracked bond lengths, bond angles, and/or chemical structures. The process also includes outputting NNFF training data comprised of the geometry error data. The NNFF training data is configured to train the NNFF for simulating molecular and/or atomic motion within the material system. The steps of this computational process may be provided as operations associated with a non-transitory computer-readable medium tangibly embodying computer readable instructions for a software program. The software program is executable by a processor of a computing device to provide the operations. The non-transitory computer-readable medium may be implemented on a simulation computer(s) of a computer system.

BRIEF DESCRIPTION OF THE DRAWINGS

FIG. 3A depicts a schematic view of a square container of water molecules where arrows depict one normal mode associated with O—H bond stretching.

FIGS. 3B and 3C depicts first and second graphs of first and second models, respectively, plotting $\Delta E_{gnnff}$ eV as a function of $\Delta E_{DFT}$, eV.

FIG. 6A depicts a graph used to calculate a weight for a target bond length using DFT on an isolated water molecule according to one embodiment.

FIG. 6B depicts a schematic diagram of S—C bond length and O—S—O bond angle used as geometry targets in a solvated sulfonate and water system.

FIG. 6C depicts a schematic diagram of O—H bond length and H—O—H bond angle used geometry targets in a liquid water system.

DETAILED DESCRIPTION

Figure 1A:
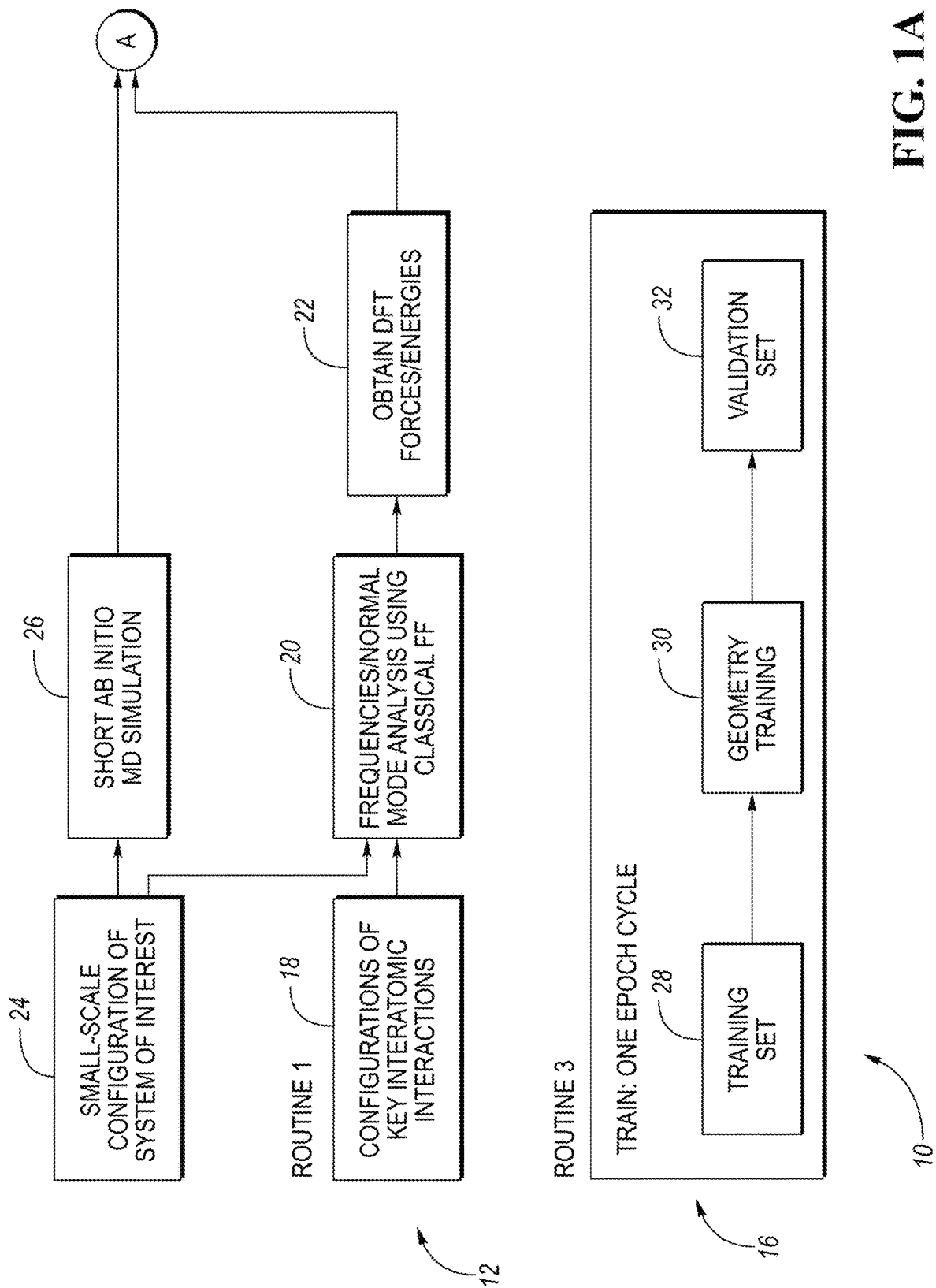
FIGS. 1A and 1B depict a schematic diagram of a training process for a neural network force field (NNFF) according to one embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Molecular dynamics (MDs) methodologies are beneficial for studying physical phenomena, such as, but not limited to, ionic transport, chemical reactions, and material bulk and surface degradation in material systems, such as, devices or functional materials. Non-limiting examples of such material systems include fuel cells, surface coatings, batteries, water desalination systems, and water filtration systems. Methodologies exist to calculate the underlying atomic forces used in the simulation of the motion of atoms. The ab initio quantum mechanics approach is very accurate but is also very expensive because a tremendous amount of computational resources is necessary to apply the approach.

Neural networks have been utilized to fit and predict quantum mechanics energies. These methodologies have been referred to as neural network force fields (NNFFs). Derivatives of energy with respect to atomic positions and forces are predicted using quantum mechanics energies. However, these methodologies are also computationally extensive.

Molecular dynamics use atomic positions (and possibly charges, bonds, or other structural information) to calculate interatomic forces of each atom, which are consequently used to modify the velocities of atoms in the simulation. The resulting trajectories of the atoms are utilized to describe physical phenomena, such as, but not limited to ionic transport in batteries and fuel cells, chemical reactions during bulk and surface material degradation, and solid-state material phase change. A tradeoff exists between the accuracy and size (measured by number of atoms and simulated dynamics time) of the simulation depending on the underlying method used to calculate the atomic forces. As set forth above, one accurate but expensive method uses the ab initio quantum mechanics approach, known as ab initio molecular dynamics (AIMD).

Atomic-scale computer simulations such as molecular dynamics (MD) provide insight into the kinetic and chemical activity of reactive systems. These insights are useful for the development of new materials. AIMD simulation methods such as density functional theory (DFT) simulation provide an accurate description of the interatomic interactions without parameter optimization for each chemical system. However, these methods are computationally expensive and are typically used for systems spanning $O(10^2)$ atoms and $O(10^2)$ picoseconds in time.

To enable such simulations on a larger scale, these interactions can be modeled using force fields (FFs). FFs may refer to a predefined set of functions mimicking the interactions observed in AIMD simulation methods. These calculations are less expensive than AIMD simulation methods, enabling simulations with more than $O(10^3)$ atoms and $O(10^5)$ picoseconds in time. Non-limiting examples of such force fields include universal force field (UFF) and reactive force field (ReaxFF). These examples rely on empirically chosen functionals for interaction potentials with tunable parameters. More recently, machine-learning (ML) and deep neural network (NN) potentials such as SchNet, fast learning of atomistic rare events (FLARE), and graph neural network force fields (GNNFF) have gained traction for allowing better accuracy than empirical force fields as the interaction functionals can be learned and modified as needed by the chemical system.

However, NN force fields (NNFFs) may have several thousand parameters that are optimized to reach the desired accuracy. Therefore, some NNFFs use greater than $O(10^3)$ training datapoints to adequately span a targeted potential energy surface (PES). For NNFFs focusing on MD or MD-like computer simulations, a proposed training method involves the sampling of an AIMD trajectory of a representative chemical system. For example, the ISO-17 database includes MD trajectories with 645,000 unique snapshots of $C_7O_2H_{10}$ isomers to train a SchNet potential. Other databases, also focusing predominantly on organic compounds, can be found on www.quantum-machine.org/datasets.

Being dependent on trajectories associated with an isolated molecule in contrast to the more realistic dense media, the ISO-17 database the www.quantum-machine.org/datasets databases present two major limitations for NNFFs. First, AIMD simulations are not sufficient to sample a targeted PES efficiently. Second, harmonic frequencies of isolated molecules do not consider intermolecular interactions.

Models such as FLARE use a Bayesian uncertainty metric to detect neighborhoods in the simulation domain. These neighborhoods are predicted with less reliability and use active learning to mitigate the error. Automation retrains such models with a single point evaluation of an uncertain structure. The automation may include training the chemical system to be very close to the actual chemical system of interest, and in some instances, the training chemical system and the actual chemical system are the same.

Therefore, many NNFF models are trained with small-scale AIMD simulations of various representative chemical systems that can describe both intra- and inter-molecular interactions of the target system. To expand sampling of the PES, AIMD may also be performed at higher temperatures. In a case where harmonic frequencies/normal modes of vibrations are considered, either an expensive DFT calculation is performed, or the structures obtained represent a less accurate FF. Consequently, either the computational cost to obtain training data or the error in the structures used increases drastically. Accordingly, there remains a need to improve current NNFF training models.

In one or more embodiments, computer processes and systems are proposed that overcome one or more of the current limitations of NNFF training identified above. The computer processes of one or more embodiments accelerates the gathering of relevant training data for NNFFs and/or improves training accuracy when data is sparse. In one or more embodiments, the computer processes and systems are generalized so that they can be applied to any material system of interest.

In one or more embodiments, one or more MD-based training schemes include one or more training structures within MD-based algorithms. The training structures of one or more embodiments may be relatively expensive to sample using ab initio or high-precision methods. Accordingly, in one or more embodiments, the training structures are generated using a lower-fidelity method such as a classical force field, and the energies are computed using a high-fidelity method such as an ab initio calculation.

In one or more embodiments, a process for training NNFFs by efficiently sampling a potential energy surface (PES) is disclosed. One or more training routines may be used to reduce a dependence on AIMD simulations. A first training routine is configured to obtain normal modes of vibration (e.g., trajectories associated with frequencies) in chemical systems including one or more molecules. The optimized geometry may be chosen using density functional theory (DFT) to bypass the computational costs associated with such AIMD simulations, whereas the normal mode displacements may be calculated using classical FFs. A second training routine is configured to isolate, solvate, and minimize high energy structures predicted by inaccurate NNFFs during a large scale MD simulations using a classical FF. In one or more embodiments, the trajectory from the minimization sampled with DFT is used for training. A third training routine is configured to penalize and minimize a geometry error and to add the penalized and minimized geometry error to a training sequence to promote an accurate structure prediction without additional datapoints. The implementation of one or more of these training routines helps to hasten the training of NNFFs by sampling targeted areas of the PES efficiently, while avoiding expensive AIMD data. The one or more training routines are sufficiently general to be implemented in any material or chemical system of interest.

One or more embodiments provide one or more training routines to efficiently train a NNFF for atomic scale simulation. The training data of one or more training routines may include atomic displacements from harmonic analysis using one or more classical force fields superimposed on an equilibrium structure obtained from DFT. The training data of one or more training routines may include spurious structures predicted by the NN that are solvated, relaxed, and corrected using classical simulations or AIMD. The actual energies may be calculated with high-fidelity ab-initio date, but the structures are generated using lower-fidelity dynamics according to one or more embodiments. The training data of one or more training routines may include penalizing geometric errors after structure optimization to ensure marked geometric targets, such as key bond lengths, are captured.

Figure 1B:
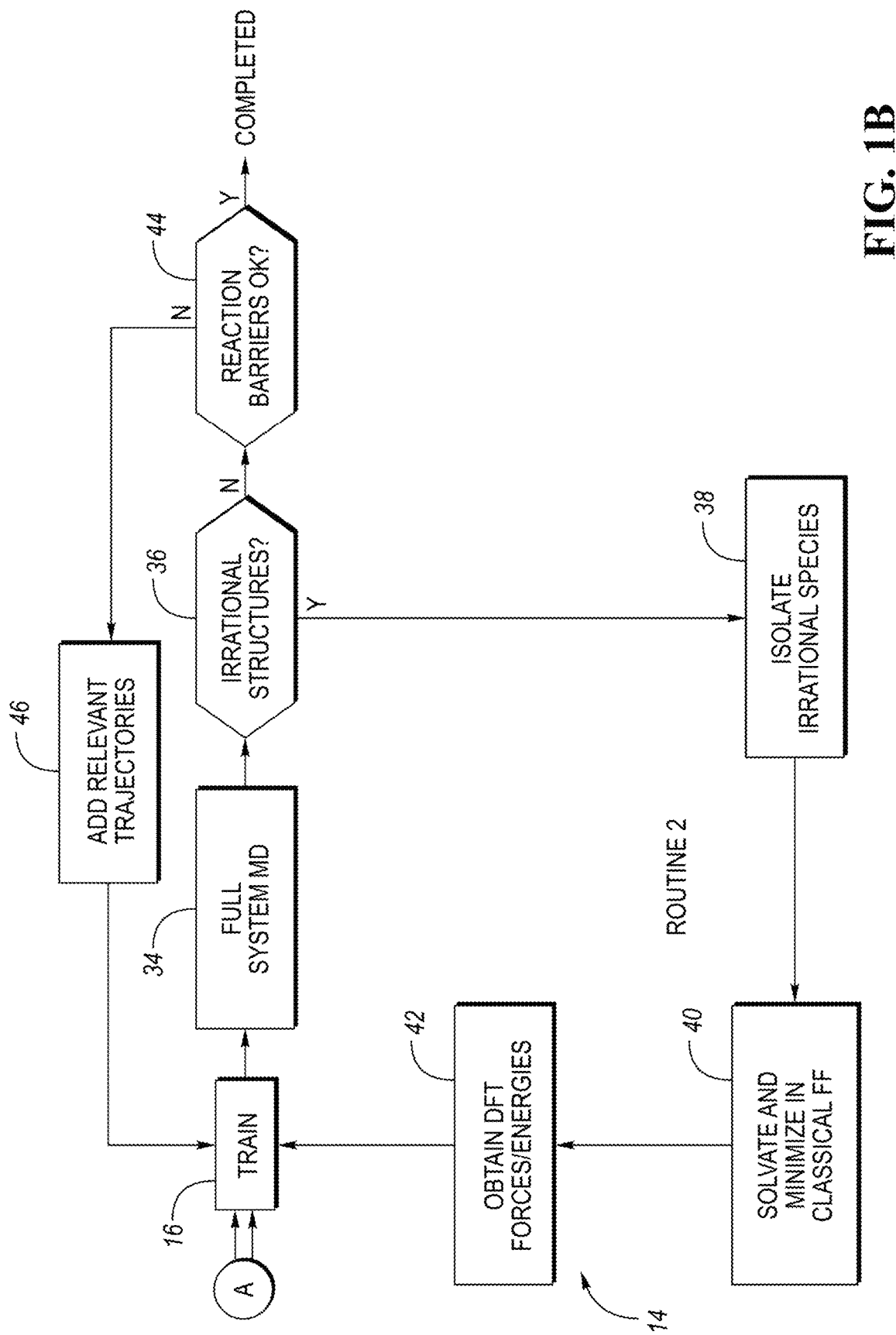

FIGS. 1A and 1B depict a schematic diagram of training process 10 for a neural network force field (NNFF) according to one embodiment. Training process 10 can be implemented on a computer system to train a NNFF. Training process 10 may be embodied in computer readable instructions that are stored in a computer module and executable by a processor.

Training process 10 includes first, second, and third training routines 12, 14, and 16. First training routine 12 corresponds to training steps based on a low-fidelity simulation. Second training routine 14 corresponds to training steps based on a low-fidelity simulation. Third training routine 16 corresponds to training steps configured to compute an error metric from a low-fidelity simulation. First, second, and/or third training routines 12, 14, and 16 may be implemented into the other steps depicted in FIGS. 1A and 1B. In one or more embodiments, training process 10 relies on the use of a classical FF. The classical FF model may include known descriptions of interactions in a chemical system. For example, the FF parameters for a Pt/sulfonates system may use ReaxFF. In other embodiments, a general FF such as UFF can be used, provided its accuracy is evaluated prior to its application, or a coarse ab initio method, such as DFT with gamma-points with low energy cutoffs.

First training routine 12 includes operations 18, 20, and 22. At operation 18, a number of configurations of key atomic interactions are determined or received. At operation 20, output from operation 18 and operation 24 is received. In one or more embodiments, operation 24 is not part of first training routine 12. At operation 24, a small-scale configuration of a chemical system of interest is determined. The small-scale configuration of a chemical system of interest is received at operation 20. At operation 20, frequencies and normal mode analysis are performed using a classical FF model. In one or more embodiments, operation 20 may use displacements from the classical FF model and/or optimal structures may be used from a DFT model. At operation 22, output from operation 20 is received and may be used by operation 22. At operation 22, DFT forces and energies are obtained.

Operation 26 receives a small-scale configuration of a chemical system of interest. Operation 26 performs a short AIMD simulation. In one or more embodiments, operation 26 is not part of first training routine 12. As shown in FIGS. 1A and 1B, third training routine 16 receives the output from operation 26. Third training routine 16 includes operations 28, 30, and 32. As shown by operations 28, 30, and 32, the output from operation 26 (e.g., a training set) is separated into a training set, a geometry training set, and a validation set, respectively. In one or more embodiments, third training routine 16 is performed by epoch cycle. The output of third training routine is received by operation 34. In one or more embodiments, operation 34 is not part of third training routine 16. Operation 34 includes performing a full system molecular dynamics (MD) analysis. In one or more embodiments, the full system is a large scale system for about 8 to 10 picoseconds (ps). The output of the full system MD analysis is received by operation 36. Operation 36 determines if one or more irrational structures relating to the chemical system are included in the full system MD analysis.

If one or more irrational structures relating to the chemical system are identified in operation 36, then second training routine 14 is performed. Second training routine 14 includes operations 38, 40, and 42. At operation 38, output from operation 34 is received. In one or more embodiments, operation 34 is not part of second training routine 14. At operation 38, one or more irrational species are isolated. At operation 40, the one or more irrational species are solvated and/or minimized using a classical FF model. At operation 42, DFT forces and/or energies are obtained after the one or more irrational species are solvated and/or minimized using the classical FF model. The DFT forces and/or energies are received by third training routine 16, and then operations 28, 30, and 32 of third training routine 16 are repeated.

If one or more irrational structures relating to the chemical system are not identified in operation 36, then training process 10 proceeds to operation 44. Operation 44 determines if the reaction barriers of the chemical system are acceptable. If the reaction barriers of the chemical system are not acceptable, then training process 10 proceeds to operation 46. Operation 46 adds one or more trajectories. Operation 46 also obtains DFT energies and/or forces if the one or more trajectories are sampled via a classical FF model. The output of operation 46 is received by third training routine 16, and then operations 28, 30, and 32 of third training routine 16 are repeated. If the reaction barriers of the chemical system are acceptable, then training process 10 is completed.

The process of calculating the frequencies of a chemical structure provides information on the correlated changes in the atomic positions leading to changes such as bond stretching or shortening and rotation of molecules, which may be significant physical data to add to a training set. However, this physical data may not be included with a molecular dynamics sampling in other embodiments. Frequency calculations may not be extracted using DFT calculations because normal-mode diagonalizations are difficult to obtain from DFT in a large system. The frequencies and the associated normal modes are a function of the second gradient in energy. Therefore, the energy convergence when using DFT for its evaluation may not be feasible for large systems. Evaluation only using a classical FF leads to erroneous trajectories. This is exacerbated when the classical FF is unreliable, and the training method does not target second gradients directly.

Figure 2:
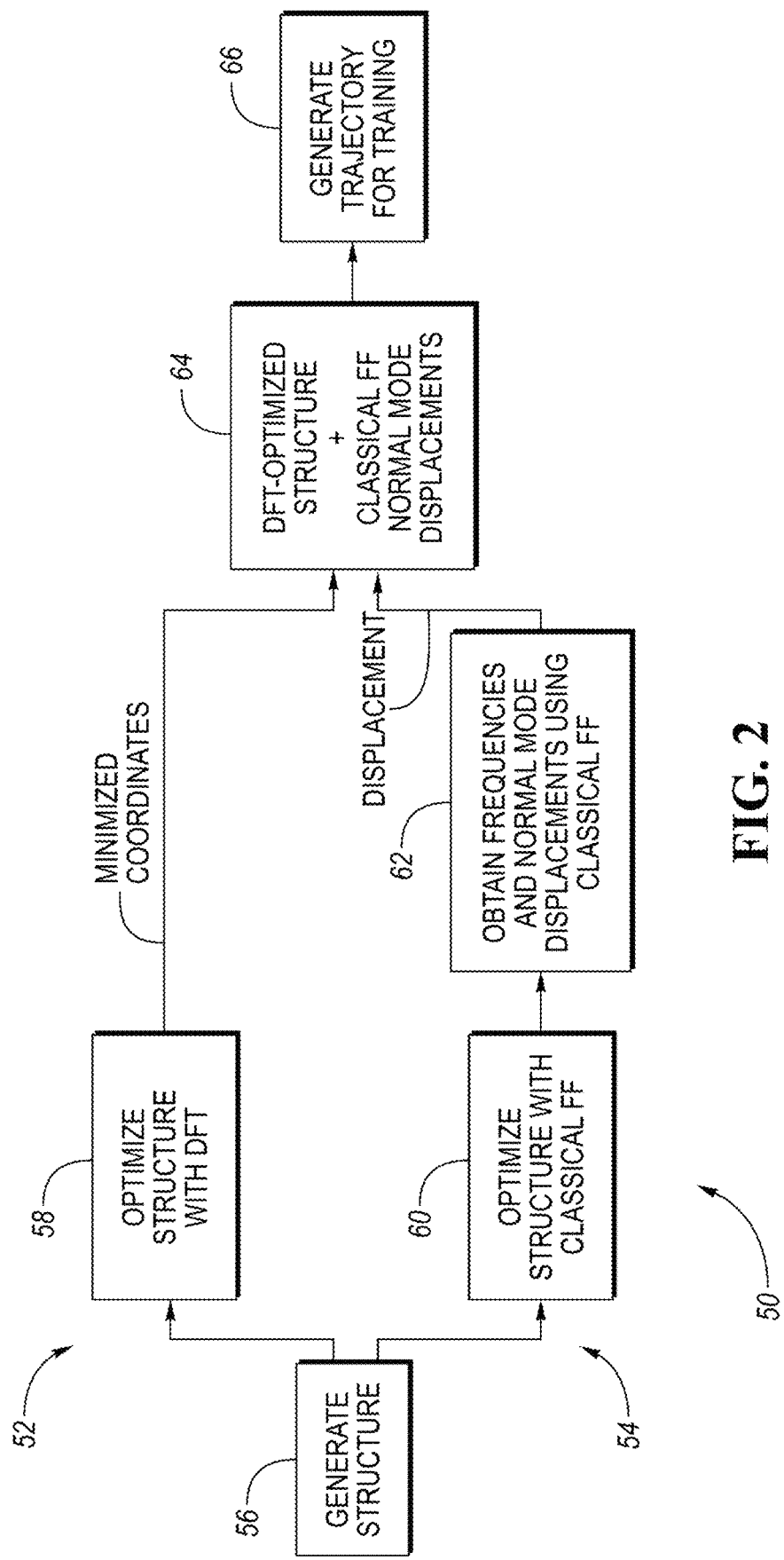
FIG. 2 depicts a schematic diagram of a process for obtaining normal modes of vibration trajectories according to one embodiment.

FIG. 2 is a schematic diagram of process 50 for obtaining normal modes of vibration trajectories according to one embodiment that addresses one or more of the shortcomings identified in the immediately preceding paragraph. Process 50 provides additional detail on the operations of first routine 12 of FIGS. 1A and 1B. Process 50 includes first and second branches 52 and 54. Before process 50 branches off into first and second branches 52 and 54, a chemical structure is generated at operation 56. First branch 52 includes operation 58. At operation 58, the chemical structure output by operation 56 is optimized using DFT to obtain a local minimum around which the PES is to be sampled with atomic displacements. Second branch 54 includes operations 60 and 62. At operation 60, the chemical structure output by operation 56 is optimized using a classical FF. At operation 62, frequencies and normal mode displacements are obtained using the classical FF based on the optimized structure predicted by the classical FF (e.g., the output of operation 60) to check whether the analysis is reasonable. In one or more embodiments, the DFT optimized structure output from operation 58 is not used. In cases where the classical FF predicts a structure with good matching to DFT, first branch 52 can be omitted.

Operation 58 of first branch 52 outputs minimized coordinates. Operation 62 of second branch 54 outputs frequency displacements. The outputs of operations 58 and 62 are received by operation 64. Operation 64 obtains a DFT optimized structure with minimized coordinates and classical FF normal mode displacements. The output of operation 64 is received by operation 66. At operation 66, training trajectories are generated using the DFT optimized structure with minimized coordinates and the classical FF normal mode displacements. In one or more embodiments, the training trajectories are obtained by applying the displacements of the frequencies from the classical FF to the DFT optimized structure.

FIG. 3A depicts a schematic view of square container 100 of water molecules 102 at 1 g cm$^{-3}$ of volume. Arrows 104 depict one normal mode associated with O—H bond stretching, with a correlation between all molecules in square container 100. FIG. 3B depicts first graph 106 of a first model, where first graph 106 plots $\Delta E_{gnnff}$, eV as a function of $\Delta E_{DFT}$, eV. The first model corresponds to a graph neural network force field (GNNFF) that was not trained with frequencies, relying only on AIMD training data. FIG. 3C depicts second graph 108 of a second model, where second graph 108 plots $\Delta E_{gnnff}$, eV as a function of $\Delta E_{DFT}$, eV. The second model corresponds to a GNNFF that was trained with frequencies (e.g., the frequencies obtained by process 50 of FIG. 2). As depicted in FIGS. 3B and 3C, first model does not distinguish between high energy states beyond about 10 eV, unlike the second model. The second model is, therefore, more reliable and can simulate higher temperatures with better accuracy according to one or more embodiments.

In one embodiment, the trajectories obtained from a low-fidelity force field include displacement amplitudes large enough to contain anharmonic contributions, allowing efficient sampling of anharmonic and yet physically reasonable trajectories. In another embodiment, the trajectories are not obtained from all normal-mode displacements, but rather from a selection thereof, such as one or more of the lowest-energy displacements (e.g., those lowest-energy displacements corresponding to an application such as ion diffusion).

In one or more early stages of an MD simulation with an FF, one or more erroneous structures may occur. Using one or more of the erroneous structures in training can often prevent incorrect reaction pathways and improve the robustness of the FF. An uncertainty metric may be used to evaluate if the prediction of properties associated with a structure is reliable. One such example is the Bayesian method used in FLARE. In case the uncertainty being high, the structure or the local neighborhood is evaluated directly with DFT and the FF is retrained with that datapoint added. This method can be successfully implemented for an arbitrary system but is generally slow because of its need to retrain at each instance of an incorrect structure and the chemical system simulated in MD must be close to the target system. Additionally, it is limited to force fields where the uncertainty of a given structure can be quantified.

In one or more embodiments, a process configured to handle such erroneous structures is disclosed. Second routine 14 includes the use of a classical FF. In one embodiment, a large-scale MD simulation is performed for about 10 picoseconds (ps) with the most updated version of the FF after training. The trajectory is then sampled to identify potentially irrational species using a simple neighborhood analysis on the domain. In this embodiment, the MD simulation is not terminated at the first occurrence of such a structure. Instead, the MD simulation evolves in the system to potentially promote more erroneous species.

In one or more embodiments, one or more of these irrational species are isolated from the system and individually solvated to capture intermolecular interactions between molecules (e.g., water molecules). The one or more solvated species are then minimized using a classical FF, such as ReaxFF, to generate a trajectory, thereby converting the high-energy unstable state to relative stability. In one or more embodiments, the classical FF can be an arbitrary choice, provided it generates a trajectory of interest. The classical FF chosen in this step need not be the same as the one used for the frequencies used in the first routine. The minimized trajectory obtained from the classical FF is then evaluated using DFT and is used for training.

This process of solvating isolated irrational species provides one or more benefits. First, the MD simulation is not stopped at an occurrence of an improbable structure, thereby allowing the simulation to evolve, to generate a better sample set of irrational structures, thereby reducing cost by avoiding retraining the FF at each stage of the MD simulation. The process of solvating isolated irrational species of one or more embodiments is transferrable to any NNFF framework and is not restricted by the formulation of a certain uncertainty metric. Second, the MD simulation does not treat a single frame containing the improbable structure, thereby allowing relaxation of the simulation under solvation to generate vital information about intermediate states in one or more reaction pathways, without isolation and neighborhood generation from the large-scale simulation. Using the process of solvating irrational species of one or more embodiments allows for faster and more efficient sampling of erroneous structures.

Figure 4A:
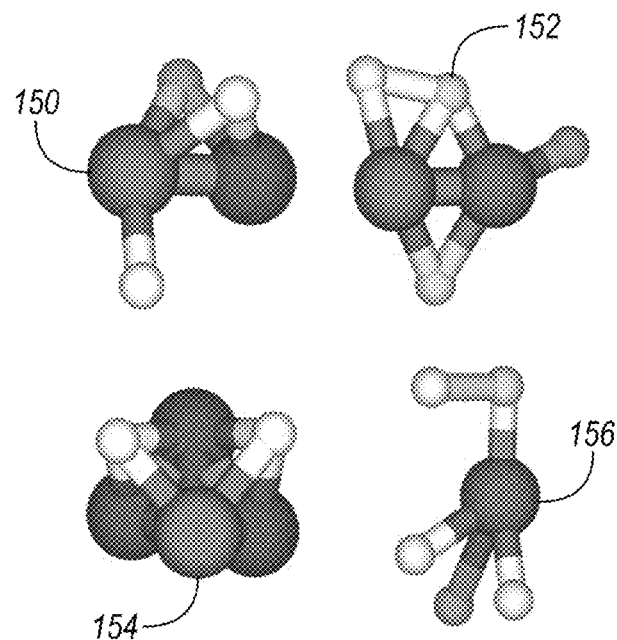
FIG. 4A depicts a schematic diagram of first, second, third, and fourth erroneous structures, with configurations of $H_3O_2$, $H_4O_2$, $H_2O_4$, and $H_5O$, respectively.
Figure 4B:
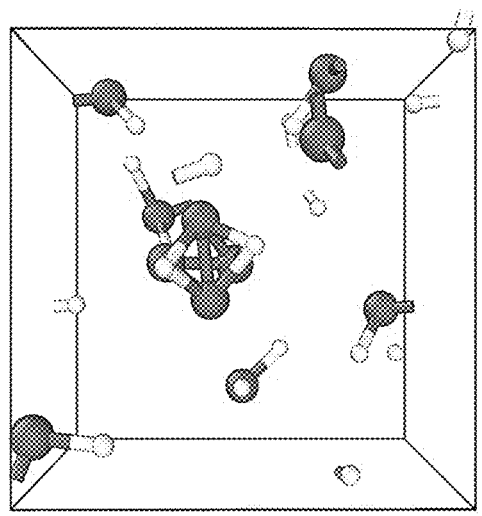
FIG. 4B depicts a schematic diagram of an initial solvated state of $H_2O_4$.
Figure 4C:
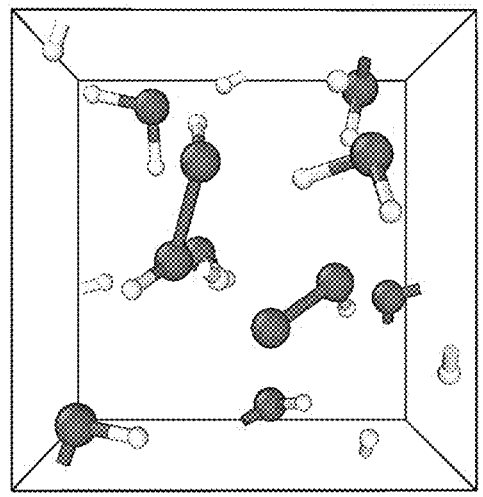
FIG. 4C depicts a schematic diagram of $H_2O_2$ and $O_2$ produced by minimization of the initial solvated state of $H_2O_4$.

FIG. 4 depicts a schematic diagram of first, second, third, and fourth erroneous structures 150, 152, 154, and 156, with configurations of $H_3O_2$, $H_4O_2$, $H_2O_4$, and $H_5O$ respectively. An early-stage FF was used to run MD simulations at 1,800K of a Pt87/Water system to yield first, second, third, and fourth erroneous structures 150, 152, 154, and 156. FIG. 4B depicts an initial solvated state of $H_2O_4$. FIG. 4C depicts $H_2O_2$ and $O_2$ produced by minimization of the initial solvated state of $H_2O_4$. Each trajectory shown in FIGS. 4B and 4C is sampled with 22 frames. Retraining the FF with the trajectories adds stability to water molecules even at high temperatures, as shown by the current species in the system after 24 ps of simulation at 1,800 K.

DFT single point calculations of structures are conventionally used for training. DFT single point calculations yield adequate results in the presence of an abundance of datapoints and sufficient sampling of the PES. However, DFT single point calculations do not perform as well when data is sparse. In a sparse-data training, the FF is introduced to a few key structures that could potentially be far away from one another in the PES. Therefore, the NNFF learns the trend required to match it accurately. However, due to the lack of an empirical functional, learning this trend is difficult. Conventionally, additional intermediate states evaluated with DFT may be included to resolve this problem.

In one or more embodiments, a geometry training routine is disclosed to penalize an error in the geometry upon minimization within the training process. One such process is third training routine 16 as shown in FIGS. 1A and 1B. In one or more embodiments, a quicker generation of an FF is enabled where the FF can ensure the equilibrium structure configuration is obtained.

Figure 5:
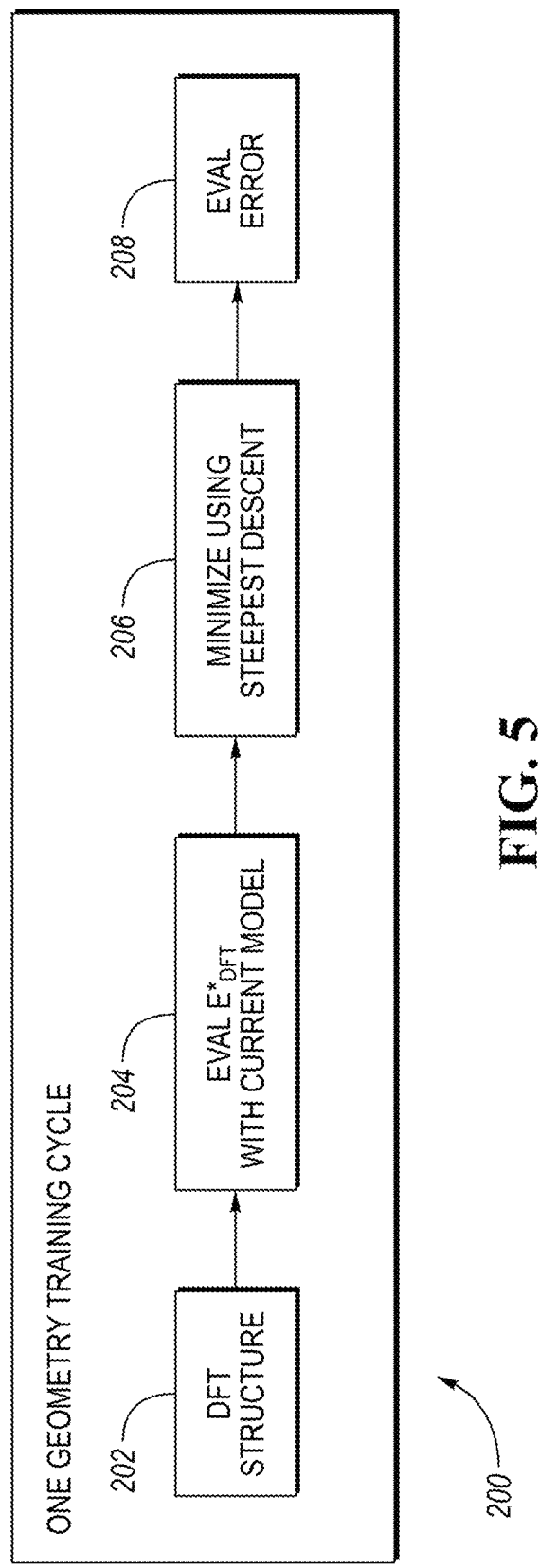
FIG. 5 depicts a schematic diagram of a geometry training routine according to one embodiment.

FIG. 5 depicts a schematic diagram of geometry training routine 200 according to one embodiment. Geometry training routine 200 depicts one geometry training cycle. At operation 202, a chemical system is optimized using DFT. As part of operation 202, one or more key bonds and angles may be marked for tracking and association with a weight for error evaluation. During training, in one or more embodiments, each structure is first evaluated with an NNFF to obtain energy $E^*_{DFT}$ as depicted by operation 204 of FIG. 5. At operation 206, minimization is performed with the NNFF using steepest descent for a maximum of 100 iterations. In one or more embodiments, the final structure is then used to evaluate the errors in bond length targets $Err_{bond}$, angle targets $Err_{angle}$ and full system energy targets $E_{struct}$ as shown as operation 208 of FIG. 5. According to one embodiment, the expressions of the evaluation of each error is given in the following equations (1), (2), and (3).

$$Err_{bond} = w_i(r_{min} - r_{DFT})^2 \quad (1)$$

$$Err_{angle} = w_j(\theta_{min} - \theta_{DFT}) \quad (2)$$

$$Err_{struct} = w_k(E_{min} - E^*_{DFT}) \quad (3)$$

where r and θ correspond to bond length and angles, with min and DFT denoting the values at the structure after minimization with the current FF and DFT-optimized structure, respectively. In the case where the current FF reproduces the correct equilibrium structure, the term denoting the difference between the states in each equation is zero. The weights, w's, are dimensional parameters that convert the difference in property to an energy unit.

FIG. 6A depicts graph 250 used to calculate a weight for a target bond length using DFT on an isolated water molecule according to one embodiment. A similar calculation may be performed for one or more bond angles. In one or more embodiments, $w_k$ may be set to one as the units correspond to energy. In one or more embodiments, the weights may be scaled to meet the type of training.

FIG. 6B depicts a schematic diagram of S—C bond length and O—S—O angle used as geometry targets in a solvated sulfonate and water system. FIG. 6C depicts a schematic diagram of O—H bond length and H—O—H angle used a geometry targets in a liquid water system.

Figure 7:
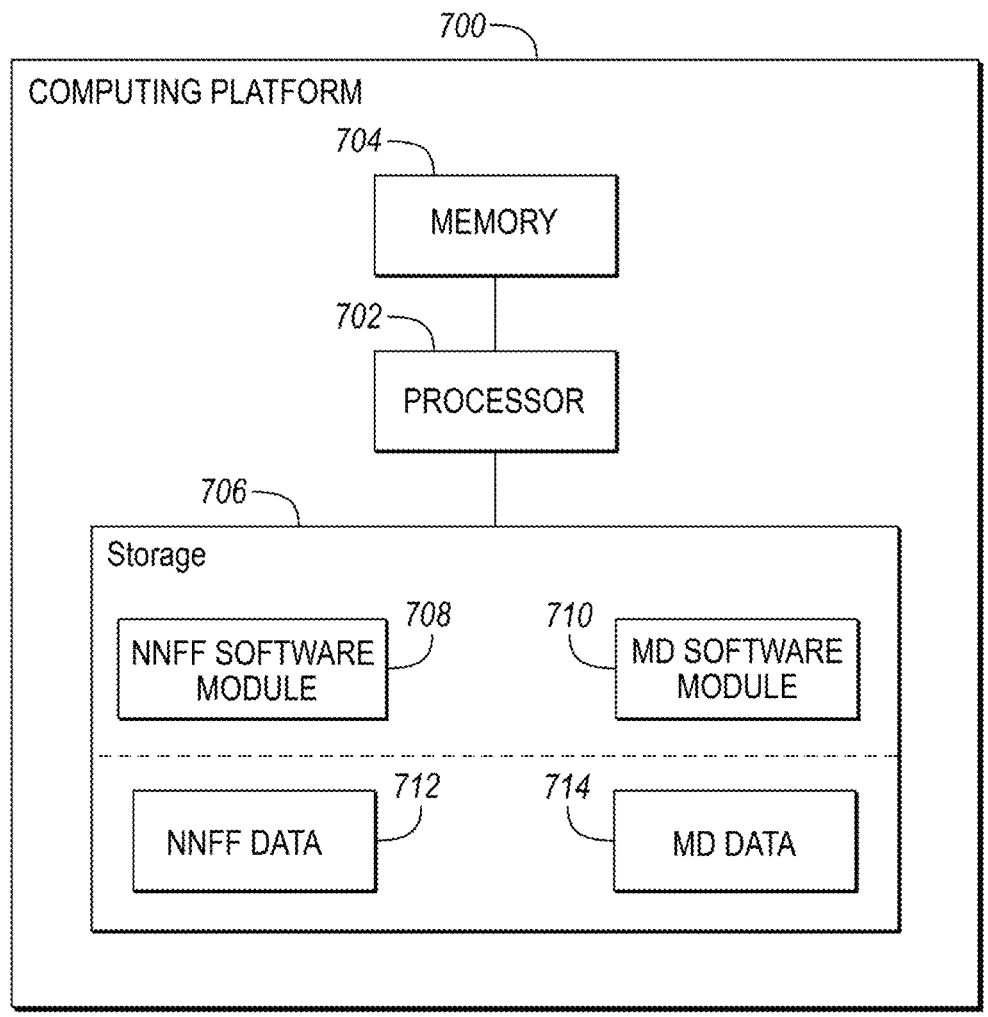
FIG. 7 is a schematic diagram of a computing platform that may be utilized to implement the NNFF algorithms of one or more embodiments, for instance, the NNFF training algorithms depicted in FIGS. 1A and 1B.

The NNFF training routines and processes of one or more embodiments are implemented using a computing platform, such as the computing platform 700 illustrated in FIG. 7. The computing platform 700 may include a processor 702, memory 704, and non-volatile storage 706. The processor 702 may include one or more devices selected from high-performance computing (HPC) systems including high-performance cores, microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory 704. The memory 704 may include a single memory device or a number of memory devices including, but not limited to, random access memory (RAM), volatile memory, non-volatile memory, static random access memory (SRAM), dynamic random access memory (DRAM), flash memory, cache memory, or any other device capable of storing information. The non-volatile storage 706 may include one or more persistent data storage devices such as a hard drive, optical drive, tape drive, non-volatile solid state device, cloud storage or any other device capable of persistently storing information.

The processor 702 may be configured to read into memory 704 and execute computer-executable instructions residing in NNFF software module 708 of the non-volatile storage 706 and embodying NNFF algorithms and/or methodologies of one or more embodiments. The processor 702 may be further configured to read into memory 704 and execute computer-executable instructions residing in MD software module 710 (such as LAMMPS) of the non-volatile storage 706 and embodying MD algorithms and/or methodologies. The software modules 708 and 710 may include operating systems and applications. The software modules 708 and 710 may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL.

Upon execution by the processor 702, the computer-executable instructions of the NNFF software module 708 and the MD software module 710 may cause the computing platform 700 to implement one or more of the NNFF algorithms and/or methodologies and MD algorithms and/or methodologies, respectively, disclosed herein. The non-volatile storage 706 may also include NNFF data 712 and MD data 714 supporting the functions, features, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

While all the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the general inventive concept.

What is claimed is:

1. A computational process for training a neural network force field (NNFF) configured to simulate molecular and/or atomic motion within a material system, the process comprising:
receiving molecular structure data of a molecule in the material system;
optimizing a geometry of the molecule using the molecular structure data and a density functional theory (DFT) simulation to obtain DFT optimized geometry data;
optimizing the geometry of the molecule using the molecular structure data and a classical force field (FF) simulation to obtain FF optimized geometry data; and
outputting NNFF training data comprised of the DFT optimized geometry data and the FF optimized geometry data, the NNFF training data is configured to train the NNFF for simulating molecular and/or atomic motion within the material system; and
training the NNFF with the NNFF training data to simulate molecular and/or atomic motion within the material system while reducing the training cost of molecular dynamics data.

2. The computational process of claim 1, wherein the FF optimized geometry data includes one or more normal mode displacements of the molecule.

3. The computational process of claim 1, wherein the classical FF simulation includes a harmonic analysis.

4. The computational process of claim 1, wherein the classical FF simulation is selected from the group consisting of: a universal force field (UFF), a classical force field, a reactive force field (ReaxFF), SchNet, fast learning of atomistic rare events (FLARE), and a graph neural network force field (GNNFF).

5. The computational process of claim 1, wherein the DFT optimized geometry data includes an equilibrium structure of the molecule.

6. The computational process of claim 1, wherein the NNFF training data includes one or more trajectories for the molecule.

7. The computational process of claim 1, wherein the material system is a portion of one of the following systems: a fuel cell, a water desalination system, a catalysis system, a coating system, and a battery system.

8. A computational process for training a neural network force field (NNFF) configured to simulate molecular and/or atomic motion within a material system, the process comprising:
receiving molecular structure data of a molecule in the material system, the molecular structure data includes an irrational structure of the molecule;
solvating the irrational structure of the molecule using a classical FF simulation or an ab initio molecular dynamics (MD) simulation to obtain solvation trajectory data of the molecule;
outputting NNFF training data comprised of the solvation trajectory data, the NNFF training data is configured to train the NNFF for simulating molecular and/or atomic motion within the material system; and
training the NNFF with the NNFF training data to simulate molecular and/or atomic motion within the material system to minimize the irrational structure predicted by MD simulations.

9. The computational process of claim 8, further comprising isolating the irrational structure of the molecule before the solvating step.

10. The computational process of claim 8, further comprising minimizing the solvation trajectory data to obtain minimized, solvation trajectory data, and the NNFF training data includes the minimized, solvation trajectory data.

11. The computational process of claim 8, further comprising obtaining one or more forces and/or energies of the molecule using a density functional theory (DFT) simulation and the solvation trajectory data.

12. The computational process of claim 8, wherein the classical FF simulation is selected from the group consisting of: a universal force field (UFF), a reactive force field (ReaxFF), SchNet, fast learning of atomistic rare events (FLARE), and a graph neural network force field (GNNFF).

13. The computational process of claim 8, wherein the irrational structure of the molecule is a predicted high energy irrational structure of the molecule.

14. The computational process of claim 8, wherein the material system is a portion of one of the following systems: a fuel cell, a water desalination system, a catalysis system, a coating system, and a battery system.

15. A computational process for training a neural network force field (NNFF) configured to simulate molecular and/or atomic motion within a material system, the process comprising:
 receiving molecular structure data of a molecule in the material system, the molecular structure data is predicted from a density functional theory (DFT) simulation, and the molecular structure data includes one or more tracked bond lengths, bond angles, and/or chemical structures;
 evaluating the molecular structure data to obtain geometry error data of the one or more tracked bonds, angles, and/or structures;
 outputting NNFF training data comprised of the geometry error data, the NNFF training data is configured to train the NNFF for simulating molecular and/or atomic motion within the material system; and
 training the NNFF with the NNFF training data to simulate molecular and/or atomic motion within the material system to promote accurate structure predictions without additional molecular dynamics simulation datapoints.

16. The computational process of claim 15, wherein the evaluating step includes evaluating the molecular structure data using the NNFF to obtain a DFT energy of the material system, the NNFF training data comprises the DFT energy.

17. The computational process of claim 15, wherein the evaluating step includes minimizing the geometry error data using the NNFF to obtain minimized geometry error data, the NNFF training data comprises the minimized geometry error data.

18. The computational process of claim 15, wherein the molecular structure data includes a weight for each of the one or more tracked bond lengths, bond angles, and/or chemical structures.

19. The computational process of claim 15, wherein the one or more tracked bonds, angles, and/or structures includes at least one bond length and at least one bond angle.

20. The computational process of claim 15, wherein the material system is a portion of one of the following systems: a fuel cell, a water desalination system, a catalysis system, a coating system, and a battery system.

* * * * *